United States Patent [19]

Williams et al.

[11] Patent Number: 5,676,967
[45] Date of Patent: Oct. 14, 1997

[54] MESH MATRIX WOUND DRESSING

[75] Inventors: Jeffrey M. Williams, Mounds View; Timothy P. Lawin, Vadnais Heights, both of Minn.

[73] Assignee: Brennen Medical, Inc., St. Paul, Minn.

[21] Appl. No.: 423,838

[22] Filed: Apr. 18, 1995

[51] Int. Cl.⁶ ............................................. A61K 9/70
[52] U.S. Cl. .................. 424/443; 424/445; 424/195.1; 424/78.06
[58] Field of Search .................. 424/443, 445, 424/195.1, 78.06; 428/224, 247, 252, 255, 265; 514/801; 530/356

[56] References Cited

U.S. PATENT DOCUMENTS

| | | | |
|---|---|---|---|
| 3,491,760 | 1/1970 | Braun et al. | 128/334 |
| 3,800,792 | 4/1974 | McKnight et al. | 128/156 |
| 3,842,831 | 10/1974 | Beisang et al. | 128/155 |
| 4,446,124 | 5/1984 | Fox, Jr. et al. | 424/27 |
| 4,456,589 | 6/1984 | Holman et al. | 424/95 |
| 4,837,024 | 6/1989 | Dov Michaeli | 424/446 |
| 4,948,651 | 8/1990 | DeBusk et al. | 422/110 |
| 4,950,699 | 8/1990 | Holman | 524/21 |
| 5,128,136 | 7/1992 | Bentley et al. | 424/443 |
| 5,135,755 | 8/1992 | Czech et al. | 424/445 |
| 5,158,772 | 10/1992 | Davis | 424/401 |
| 5,324,775 | 6/1994 | Rhee et al. | 525/54.2 |
| 5,328,449 | 7/1994 | Andrews et al. | 602/42 |
| 5,330,483 | 7/1994 | Heaven et al. | 606/114 |
| 5,340,363 | 8/1994 | Fabo | 604/304 |

FOREIGN PATENT DOCUMENTS

| | | |
|---|---|---|
| PCT/GB94/00114 | 4/1994 | WIPO . |
| PCT/GB94/00291 | 6/1994 | WIPO . |

OTHER PUBLICATIONS

Fulcher, R. Gary, Oat Beta_D_Glucans: measurement and assurance of physical characteristics, Univ. of Minnesota, 1995.

DuPont Hytrel Design Guide—Mopdule V, 1995.

Primary Examiner—Thurman K. Page
Assistant Examiner—Sharon Howard
Attorney, Agent, or Firm—Moore & Hansen

[57] ABSTRACT

A wound dressing for covering a wound to the body, providing slow release of a combination of collagenic protein and oligosaccharide, enhancing vapor transmission from the wound, and enhancing healing comprises an aqueous combination of collagen and oligosaccharide coated on a mesh surface and dehydrated to a low moisture content. The ratio of oligosaccharide to collagenic protein ranges from 1:100 to 100:1, with a content (dry basis) of collagen at about 0.1 to 30 percent and oligosaccharide in the dressing at about 0.1 to 20 percent.

18 Claims, 1 Drawing Sheet

MESH MATRIX WOUND DRESSING

BACKGROUND OF THE INVENTION

This invention relates generally to dressings for the treatment of wounds. More particularly, this invention pertains to flexible dressings for speeding the recovery from burn wounds, ulcers, donor sites and other shallow wounds.

Each year, approximately 2.4 million Americans are burned. Physicians treat about 650,000 of the burn victims, 75,000 of these patients require hospitalization, and 12,000 die of burns. One million people each year sustain substantial temporary or permanent disabilities resulting from burn injuries.

When skin is damaged or missing due to burns, trauma or toxic injury, the mechanical functions of the skin must be replaced promptly to provide an environment which will optimize cellular regeneration and minimize the chance for sepsis so that healing will ensue. Wound healing is a complex biological process that involves the integration of inflammation, mitosis, angiogenesis synthesis and remodeling of the cellular matrix.

The survival rate of burn victims has dramatically increased during the past ten years, thereby creating a need for devices that assist in the recuperative process.

An ideal dressing is one which flexibly covers the wound site and provides (a) a barrier to infectious organisms, (b) absorptive capacity for excess exudate, (c) control of wound desiccation, (d) an environment which promotes the healing process, and (e) a decrease in pain by covering the exposed nerve endings.

Both biological and synthetic dressings serve as temporary coverage for partial thickness wounds and essentially all claim to provide a barrier that provides the optimum environment for healing. Among the biological dressings, pigskin, i.e. porcine xenografts, have been the dressing of choice since the early 1960's. Porcine xenograft functions, on a temporary use basis, similarly to the patient's own skin in providing a moisture retaining, germ resistant covering while possibly stimulating the healing process by being a heterologous tissue. There also may be an immunostimulation at the wound site due to the presence of heterologous collagen, glycoproteins, polysaccharides and other cell wall constituents in the porcine epidermis, corpus striatum and dermis. However, no claims have been made for the use of porcine dressings to enhance healing.

Therapeutic benefits from naturally occurring agents have been found in many disciplines of medicine. The opium poppy, from which morphine and its analogues are derived, and foxglove, yielding digitalis, are prime examples. Herbs, plant and plant gums or extracts have been used for centuries. Aloe vera gums, cereal gums and oat baths are recognized treatment moieties.

Collagen is the main structural component of connective tissue. It may be extracted from connective tissue and bones from bovine, porcine or other mammalian sources. Collagen sponges have been used clinically in dentistry. Collagen has also been a principal component of products intended for tissue repair, cartilage replacement and wound therapy.

U.S. Pat. No. 4,950,699 of Holman discloses a formulation for a wound dressing comprising a mixture of collagen and an acrylic adhesive.

Wound therapy products have been marketed by Dow B. Hickam, Inc. of Sugarland, Tex. under the trademark Biobrane II, by BioCore of Kansas City, Mo. under the trademark SkinTemp, and by Inamed of Bristol, England under the trademark Spenco 2nd Skin.

However, none of these dressings is known to provide any type of pharmacological stimulation to the wound.

BRIEF SUMMARY OF THE INVENTION

The invention is a wound dressing comprising a hydrocolloid sheet being a matrix of two biologically derived components, carried by a semi-occlusive film-backed multifilament or monofilament polyester mesh sheet.

The dressing is intended for use as a temporary dressing on partial thickness burns, ulcers, donor sites and other shallow wounds.

By definition, a hydrocolloid is a substance that forms a gel in the presence of an aqueous solution and is in a state of division preventing passage through a semi-permeable membrane. A hydrocolloid consists of particles too small for resolution with an ordinary light microscope, and in suspension or solution, fails to fall out and is light-diffractive.

One particular form of the invention is a casted polyester mesh dressing that has been treated with an oligosaccharide such as beta-D-glucan or hyaluronic acid and with a collagen or similar fibrous protein. The oligosaccharide and collagen are applied to a fibrous mesh netting as an aqueous solution and dehydrated. A vapor permeable film of plastic material occlusive to moisture and bacteria is joined to one side of the impregnated mesh netting to form an external surface of the dressing. The cast dressing is then cut to the desired size of individual dressings.

The combination of an oligosaccharide and a collagenic material in a dressing has been found to provide numerous benefits, including decreased healing time, the maintenance of optimum moisture content at the wound surface, decreased pain, decreased fluid loss, decreased exudative protein loss, reduced heat loss, enhanced blockage of contaminating bacteria, and enhanced facilitation of movement.

A BRIEF DESCRIPTION OF THE DRAWING

The single FIG. 1 is a side view of a wound dressing according to the present invention.

DESCRIPTION OF THE PREFERRED EMBODIMENTS

Figure 1:
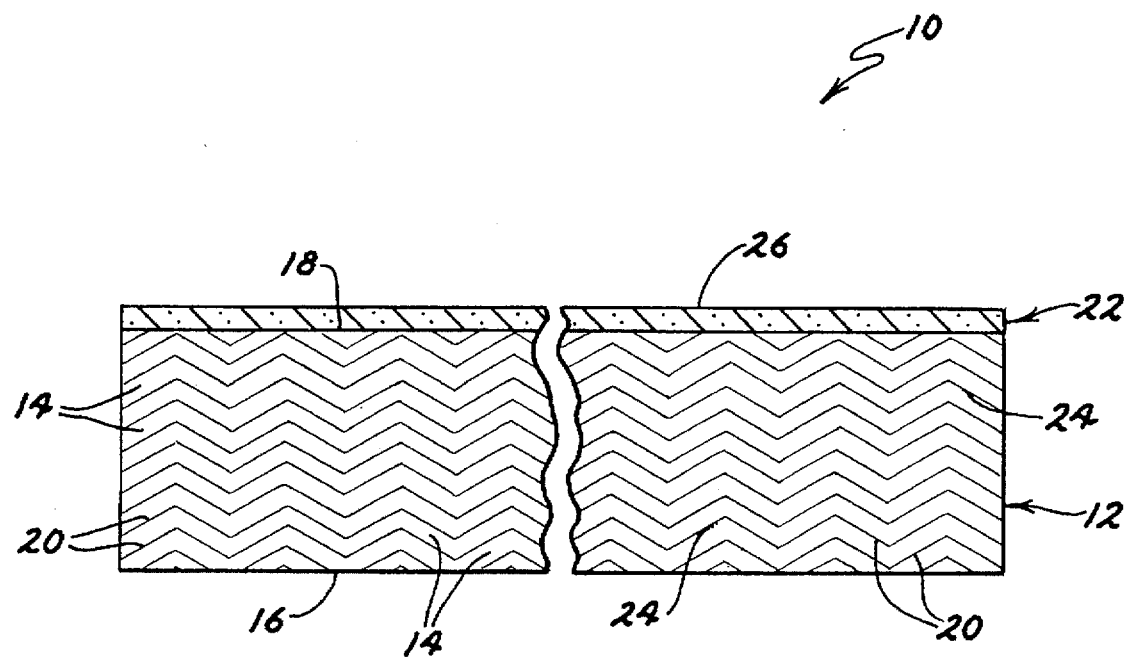

The matrix-type wound dressing 10 according to the present invention is readily formed from commercially available materials.

As shown in the figure, a mesh netting material is used as the dressing substrate, and may be a plastic material. A material which has been found to work well is a multifilament woven mesh formed of thin polyester fibers 20. The mesh netting 12 has holes or openings 14 of about $\frac{1}{32}$ inch, and the structure of the netting 12 permits a solution of oligosaccharide such as glucan and a collagen to impregnate and fill the openings 14. The impregnated netting is then dehydrated and oligosaccharide and collagen are deposited and adhere to the fibers 20. Following dehydration, the mesh netting 12 has sheet-like planar surfaces 16 and 18 formed of fiber surfaces and an interstitial, substantially uniformly deposited mixture 24 of oligosaccharide and collagenic proteins.

The top covering of the dressing 10 comprises a vapor permeable layer 22 which is occlusive to moisture and bacteria. A thin film of butylene/poly(alkylene ether) phthalate plus stabilizer has been found useful as the layer 22, providing a moisture barrier and bacteria barrier while allowing vapor to pass through the dressing from the wound site into the air. The layer 22 is joined to a surface 18 of the netting 12 by a thermal process or other means to provide an external surface 26. The uncovered surface 16 of the mesh netting 12 becomes the surface to be in contact with the wound site. Exemplary covering films are manufactured by E. I. Dupont de nemours, Wilmington, Del. as HTR8171 and HTR8206 under the trademark Hytrel. While a film thickness of 1 mil (0.001 inch) has been found to work well, it is anticipated that the film thicknesses in the range of 0.75 to 2 mils may be used.

The oligosaccharide found most useful in the present invention is beta-D-glucan. It is a biological compound found in essentially all living cells. It is a highly branched homopolysaccharide with B(1-6)-linked side chains and is isomerically diaposed to alpha-poly-D-glucose and therefore non-functional as a structural support component of the cell. Beta-glucan has been investigated as a potential biological response modifier and it may be a macrophage stimulator.

The primary sources of beta-glucan have been from yeast and bacterial cells. Oat-derived beta-glucan is commonly used as a component of cosmetic and skin care products, being a moisturizing agent that has cleansing, soothing and anti-pruretic activity.

Collagen is commercially available in several forms. While other collagenic protein materials may be used, a readily available material is a lyophilized, soluble, collagen fiber-like powder extracted from bovine hides. It is a mixture of Type I and Type III collagens. Type II and/or Type IV collagens may also be used, but their lower solubility, higher hydrophobicity makes their controllable application as a suspension to fibers more difficult, and their subsequent transport into the wound proceeds at a lower rate.

An aqueous based mixture of the oligosaccharide and collagen for impregnating the mesh netting 12 may contain about 1-10 percent oligosaccharide and 1-15 percent collagen. The mixture is applied to the mesh netting 12 to substantially impregnate it. Dehydration, preferably at superatmospheric pressure and elevated temperature, provides a dressing 10 in which the collagen is about 0.1-20 percent (dry basis) of the dressing weight, and the oligosaccharide is about 0.1-15 percent (dry basis) of the dressing weight.

Preferably, the dressing includes about 5-20 percent collagen and 5-10 percent oligosaccharide (dry basis).

EXAMPLE

A polyester woven multifilament mesh netting having a thickness of 0.020 inch was obtained. The netting had an average "hole" size of about 1/32 inch.

An aqueous-based solution of oat-derived beta-D-glucan and bovine collagen containing Type I and Type III collagens was prepared. The solution contained 2% glucan and 3% collagen.

The aqueous solution was coated on the mesh netting and adhered to the fibers of the netting.

The coated netting was then subjected to dehydration at about 40 degrees C. Following dehydration, one side of the coated netting was thermally bonded to a 1 mil thickness of vapor-permeable Hytrel butylene/poly(alkylene ether) phthalate film.

The weight percentages of the components of the dressing were as follows:

| | |
|---|---|
| beta-D-glucan (oat-derived) | 7.9 |
| collagen (bovine hide, Types I, III) | 10.0 |
| Hytrel-based polymeric film | 27.6 |
| polyester mesh netting (0.020 inch) | 54.5 |
| total | 100.0 |

The dressing described above provides an optimum gas permeable, semi-occlusive transmitting environment to the wound site. It reduces pain by providing a cover for sensory nerve terminals. The dressing reduces or eliminates the need for painful dressing changes. Losses of fluid and exudative protein are decreased. Heat loss is decreased. The dressing forms a barrier against bacterial or other contamination. The dressing remains flexible and facilitates movement, promoting early physical therapy.

It is anticipated that various changes and modifications may be made in the construction of the wound dressing disclosed herein without departing from the spirit and scope of the invention as defined in the following claims.

For example, a sponge or other substrate may replace the mesh netting, where medically appropriate and if its properties match the desired end.

What is claimed is:

1. A wound dressing comprising:

a polyester mesh netting;

a coating on said polyester mesh netting comprising a mixture of beta-D-glucan and a collagen; and a polymeric film bonded to one side of said coated polyester mesh netting.

2. The wound dressing of claim 1, wherein said beta-D-glucan is extracted from oats and applied to said mesh netting to produce a concentration equal to about 0.1-5 percent of the dressing dry weight.

3. The wound dressing of claim 1, wherein said collagen comprises a mixture of Type I and Type III collagens, said collagen mixture comprising 0.1-20 percent (dry weight) of the dressing.

4. The wound dressing of claim 1, wherein said polymeric film comprises a high vapor permeable material.

5. The wound dressing of claim 1, wherein said polymeric film comprises a stabilized butylene/poly (alkylene ether) phthalate material.

6. The wound dressing of claim 1, wherein said collagen comprises a bovine hide extract.

7. The wound dressing of claim 1, wherein said dressing comprises:

| Component | Percent, dry basis |
|---|---|
| Beta-D-glucan | 0.1-15 |
| Collagen, bovine | 0.1-20 |
| Stabilized butylene/poly(alkylene ether)phthalate film | 12-36 |
| Polyester mesh netting | 30-85. |

8. A wound dressing, comprising:

| Compound | Percent, dry basis |
|---|---|
| Beta-D-glucan | 5-10 |
| Collagen, bovine | 5-20 |
| Stabilized butylene/poly(alkylene ether)phthalate film | 24-36 |

-continued

| Compound | Percent, dry basis |
| --- | --- |
| Polyester mesh netting, about 0.02 inch diameter filaments, about 1/32 inch opening size | 45–65. |

9. The wound dressing of claim 1, wherein said beta-D-glucan is extracted from a cereal grain.

10. The wound dressing of claim 1, wherein said polymeric film has a thickness of about 0.001 inch +/− about 0.0005 inch.

11. The wound dressing of claim 4, wherein said polymeric film comprises a stabilized butylene/poly(alkylene ether) phthalate material sold by E. I. Dupont de Nemours under the trademark Hytrel.

12. The wound dressing of claim 4, wherein said polymeric film comprises a stabilized butylene/poly(alkylene ether) phthalate material sold by E. I. Dupont de Nemours as one of Hytrel Grade HTR8181 and Hytrel Grade HTR8206.

13. A wound dressing comprising:
   a polyester mesh netting formed of woven multifilament polyester;
   a deposit on said mesh netting filaments comprising a mixture of a cereal-derived beta-D-glucan and a collagen in a ratio of 1:100 to 100:1 (dry basis); and
   a polymeric film of high vapor permeable material bonded to one side of the coated mesh netting to comprise an exterior surface of said wound dressing.

14. The wound dressing of claim 13, wherein said polymeric film comprises a stabilized butylene/poly(alkylene ether) phthalate material.

15. The wound dressing of claim 13, wherein said polymeric film is occlusive of bacteria and substantially impermeable to moisture.

16. A method for preparing a wound dressing, comprising:
   forming a laminar mesh netting of a filamentous plastic material, said netting having interstitial spaces for receiving and retaining a gel;
   attaching one side of said laminar mesh netting to a film generally occlusive to bacteria and liquid water and generally permeable to gases;
   preparing a liquid aqueous mixture of collagen and cereal-derived beta-D-glucan;
   applying said liquid aqueous mixture to said laminar mesh netting to fill said interstitial spaces; and
   drying said applied mixture to form a continuous gel of collagen and beta-D-glucan in a mesh matrix having an occlusive backing film, for application to a wound.

17. The wound dressing of claim 13, wherein said netting has a thickness of about 0.01–0.05 inches.

18. The wound dressing of claim 1, wherein said mesh netting is a woven, multifilament material having openings forming interstices in which the mixture of beta-D-glucan and collagen is substantially, uniformly deposited.

* * * * *